United States Patent [19]
Archer

[11] Patent Number: 5,771,270
[45] Date of Patent: Jun. 23, 1998

[54] COLLIMATOR FOR PRODUCING AN ARRAY OF MICROBEAMS

[76] Inventor: David W. Archer, 486 Penhill Avenue, Ottawa, Ontario, Canada, K1G 4E1

[21] Appl. No.: 813,547

[22] Filed: Mar. 7, 1997

[51] Int. Cl.[6] ...................................................... A61N 5/10
[52] U.S. Cl. ............................................. 378/65; 378/150
[58] Field of Search .............................. 378/64, 65, 145, 378/147, 149, 150

[56] References Cited

U.S. PATENT DOCUMENTS

| | | | |
|---|---|---|---|
| 1,476,048 | 12/1923 | Bucky . | |
| 2,139,966 | 12/1938 | Loebell | 250/94 |
| 2,624,013 | 12/1952 | Marks | 250/105 |
| 2,638,554 | 5/1953 | Bartow et al. | 250/99 |
| 4,726,046 | 2/1988 | Nunan | 378/65 |
| 4,827,491 | 5/1989 | Barish | 378/65 |
| 4,856,043 | 8/1989 | Zola | 378/149 |
| 4,951,305 | 8/1990 | Moore et al. | 378/147 |
| 5,012,088 | 4/1991 | Cole et al. | 350/227.19 |
| 5,012,506 | 4/1991 | Span et al. | 378/152 |
| 5,054,048 | 10/1991 | Wang | 378/146 |
| 5,195,120 | 3/1993 | Evain et al. | 378/154 |
| 5,220,174 | 6/1993 | Oshida et al. | 250/505.1 |
| 5,339,347 | 8/1994 | Slatkin et al. | 378/65 |
| 5,351,280 | 9/1994 | Swerdloff et al. | 378/65 |
| 5,436,958 | 7/1995 | Taylor | 378/149 |
| 5,479,469 | 12/1995 | Fraser et al. | 378/149 |
| 5,555,283 | 9/1996 | Shiu et al. | 378/150 X |
| 5,596,619 | 1/1997 | Carol | 378/150 X |

*Primary Examiner*—David P. Porta
*Attorney, Agent, or Firm*—Litman, McMahon & Brown, LLC

[57] ABSTRACT

A collimator for producing an array of non-overlapping parallel microbeams of radiation of adjustable width, from a single wide beam of radiation. The invention comprises two grid assemblies arranged in juxtaposition with each other, each comprising a number of alternating parallel leaves of contrasting X-ray permeability. Each leaf of one grid assembly is of substantially the same thickness as the corresponding leaf of the other grid assembly such that passage of a wide beam of radiation through the grid assemblies results in microbeams of radiation. By offsetting the two grid assemblies slightly, the width of the microbeams may be altered. A housing apparatus is provided to ensure the leaves within one grid assembly remain parallel to one another, and that the leaves of one grid assembly remain parallel to those of the other. A micrometer adjustment apparatus allows precise control of the position of one grid assembly in relation to the other.

24 Claims, 6 Drawing Sheets

COLLIMATOR FOR PRODUCING AN ARRAY OF MICROBEAMS

FIELD OF THE INVENTION

The invention relates to a collimator for producing non-overlapping microbeams of X-rays from a single wide beam of X-rays.

BACKGROUND OF THE INVENTION

The use of multiple non-overlapping microbeams of high energy electromagnetic radiation for radiation therapy is a known process. The target tissue, usually a tumor, is subjected to a number of closely-spaced microbeam radiation exposures, such that the tissue exposed to the microbeams receives a radiation dosage exceeding the maximum dose that such tissue can survive, while the tissue between the microbeams is left relatively healthy. The microbeams are usually applied more than once from different angles such that the target tissue receives a higher dosage of the radiation than does non-target tissue. The result is that the target tissue is substantially destroyed while the non-target tissue is left relatively healthy.

It has been shown that certain types of cells, notably endothelial cells lining blood vessels, have the capacity to migrate over microscopic distances, infiltrating tissue damaged by radiation and reducing tissue necrosis in the beam path. Thus, by using microbeams whose individual widths are typically in the order of 20 to 200 micrometers, and spacing them about 50 to 500 micrometers apart, sufficient unirradiated or minimally irradiated microscopic zones remain in the non-target regions to allow efficient repair of irradiation-damaged tissue, facilitating recovery of the tissue in these regions.

In the past, a single beam having either a circular cross-section, or an elongated rectangular cross-section has been used in performing microbeam therapy. However, this has been found to be time consuming, due to the necessary repetitive steps of applying one beam, and then moving the beam a precise microscopic distance before applying the next beam.

A further problem with the current practice is in the inability to vary the width of the microbeams. It has been found that it is desirable to make the microbeam widths variable according to the susceptibility of the target tissue and the surrounding tissue to irradiation, and the capacities of the various involved tissues to regenerate. By varying the microbeam widths according to these factors, the microbeam therapy may be optimized to facilitate the healing process.

U.S. Pat. No. 5,339,347 granted on Aug. 16, 1994 to Slatkin discloses a method of performing microbeam therapy. Although the patent speaks of using a collimator to produce the array of beams simultaneously, it presents no suggestion as to how such a collimator might be constructed. While the patent further relates the desirability of varying the width of the microbeam, it merely states the problem without suggesting the solution.

U.S. Pat. No. 5,220,174 granted on Jun. 15, 1993 to Oshida discloses an apparatus for controlling the dose of irradiation for surface treatment or material treatment of an assembly line product as it passes under the irradiator on a conveyor. Among other embodiments, the patent describes the use of two barrier bodies having the same configuration juxtaposed vertically. The configuration of each of these bodies is such that they describe a plurality of parallel elongated orifices. These bodies may be shifted relative to each other in a horizontal direction so as to increase, or decrease the amount of radiation striking the products passing under the irradiator. Although this patent does allow for the simultaneous application of an array of beams of adjustable width, the apparatus described cannot be translated to a micro-dimensional scale. If the apparatus disclosed were to be scaled down to the dimensions required in micro-beam X-ray treatment, the thickness of those portions purporting to serve as a barrier to the X-rays in the direction of the X-ray beams would be insufficient to effectively attenuate the X-rays. Even if the thickness of the apparatus were to be increased significantly in the direction of the X-rays, it has been shown that it is extremely difficult to retain the perfect parallelism among extremely thin barrier bodies, necessary to allow precise beams of rays to pass through. Furthermore, the patent discloses no apparatus or method by which the translation of the barrier bodies relative to one another may be controlled or measured.

U.S. Pat. No. 1,476,048 granted on Dec. 4, 1923 to Bucky discloses an apparatus for filtering out secondary X-rays arising when X-rays pass through a body, to prevent blurring of photographs produced by the primary X-rays. This is achieved by using a fine grid of parallel leafs which allow X-rays parallel to the direction of the primary X-rays to pass through the grid, but blocks any X-rays not parallel to the primary X-rays. The patent discloses a grid made of alternating layers of thin leaves of metal impervious to X-rays and celluloid leaves which are relatively translucent to X-rays and pressing them together using pressure. The purpose of the device is to block non-parallel radiation while minimizing the effect of any blockage of X-rays on the photograph. Although this patent does disclose the use of a fine grid of alternating materials of contrasting X-ray permeability, the function and effect of the grid is to affect the flow of X-rays parallel to the leaves of the grid as little as possible, and is thus not useful in creating discrete microbeams of X-rays separated by distinct spaces in which little or no X-rays fall. Further, there is no disclosure of any means by which the width of the X-ray permeable portions of the grid may be altered. No dimensions for the leaves are provided.

SUMMARY OF THE INVENTION

According to a broad aspect, the invention provides a collimator comprising a grid assembly of a plurality of alternating parallel leaves of contrasting X-ray permeability, and supporting means by which the grid assembly is rigidly supported such that the leaves of the grid assembly are rigidly held parallel to one another.

According to another aspect, the invention provides an adjustable collimator comprising two grid assemblies arranged in juxtaposition with each other, each comprising a plurality of alternating parallel leaves of contrasting X-ray permeability, each leaf of one grid assembly being of the same thickness as the corresponding leaf of the other grid assembly; supporting means by which each of said grid assemblies is rigidly supported such that the leaves of each grid assembly are rigidly held parallel to one another, and the leaves of one grid assembly remains substantially parallel to the leaves of the other grid assembly; and adjustment means by which the grid assemblies may be precisely mutually displaced in a linear direction perpendicular to the leaves of the grid assemblies.

Advantageously, the invention allows an operator to simultaneously apply an array of non-overlapping microbeams of radiation. Further, a second embodiment of the invention allows the operator to control and monitor the widths of these microbeams with a high degree of precision.

BRIEF DESCRIPTION OF THE DRAWINGS

Preferred embodiments of the invention will now be described with reference to the attached drawings in which.

DETAILED DESCRIPTION OF THE PREFERRED EMBODIMENTS

Figure 1:
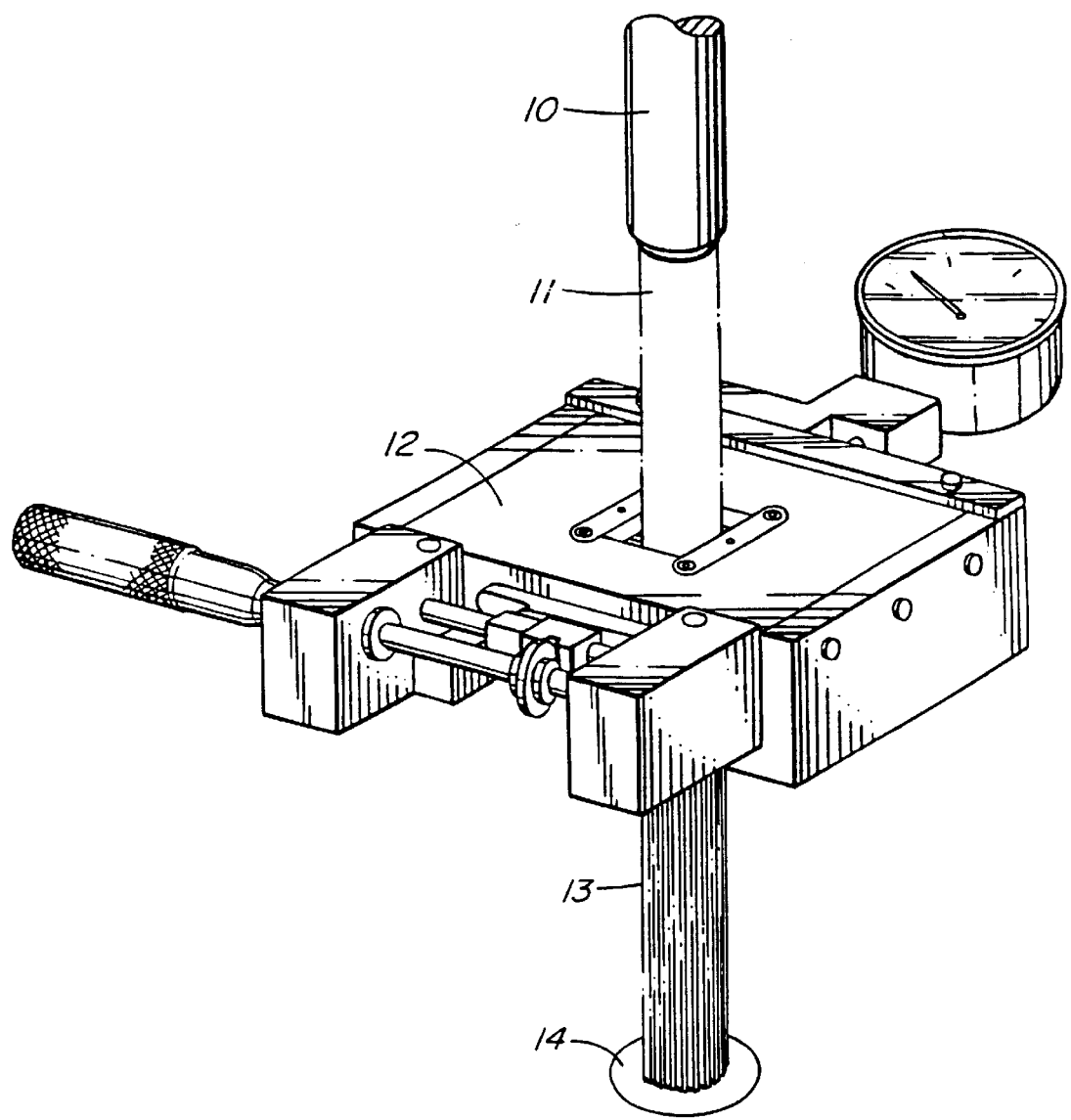
FIG. 1 is a schematic view of a microbeam radiation therapy system including a microbeam collimator according to the invention.

FIG. 1 shows a horizontally oriented microbeam collimator apparatus 12 according to the invention, in use in a microbeam radiation therapy system. A radiation source 10 produces a wide beam of radiation 11 which, as it passes through the microbeam collimator apparatus 12 is collimated into a plurality of non-overlapping microbeams of radiation 13 which strike a target 14. Although the microbeam collimator apparatus 12 is shown in a horizontal orientation, other orientations are possible, vertical for example.

Figure 2A:
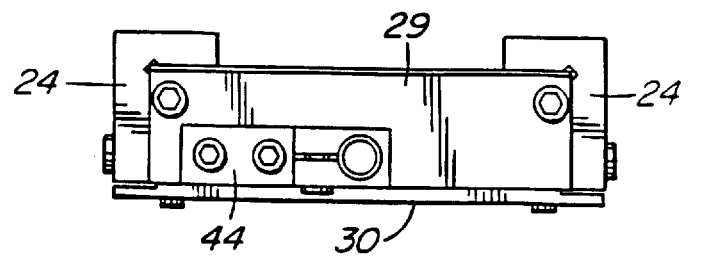
FIG. 2a is a top view of the collimator of FIG. 2 with the microbeam width indicator removed.
Figure 2:
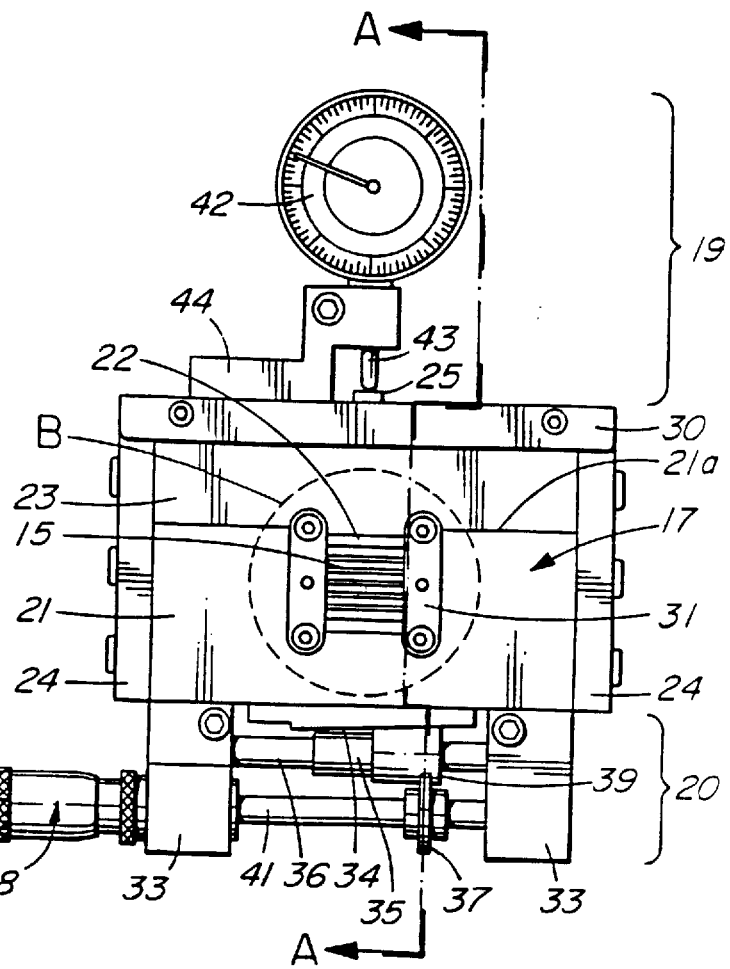
FIG. 2 is a front view of a preferred embodiment of a collimator according to the invention.
Figure 2B:
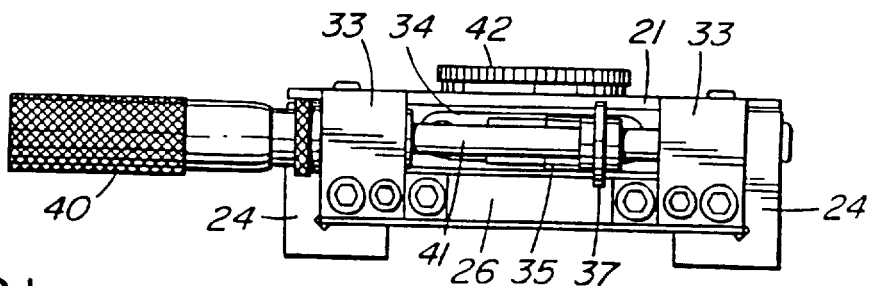
FIG. 2b is a bottom view of the collimator of FIG. 2.
Figure 3:
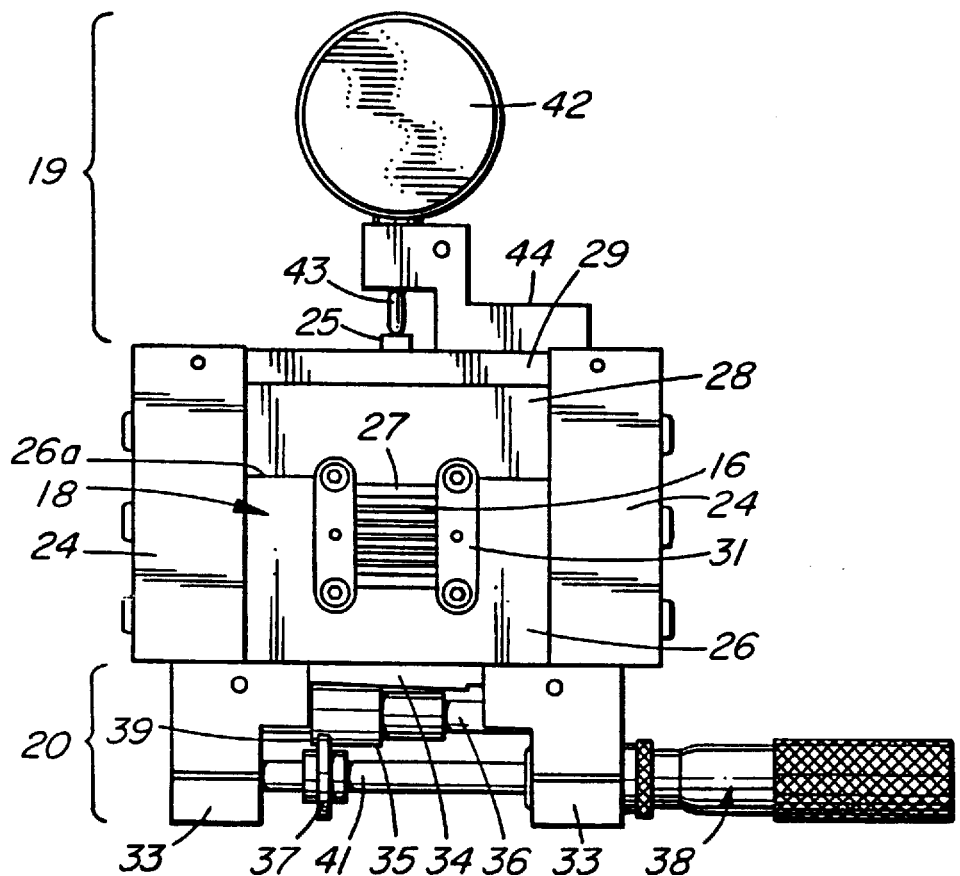
FIG. 3 is a rear view of the collimator of FIG. 2.
Figure 4:
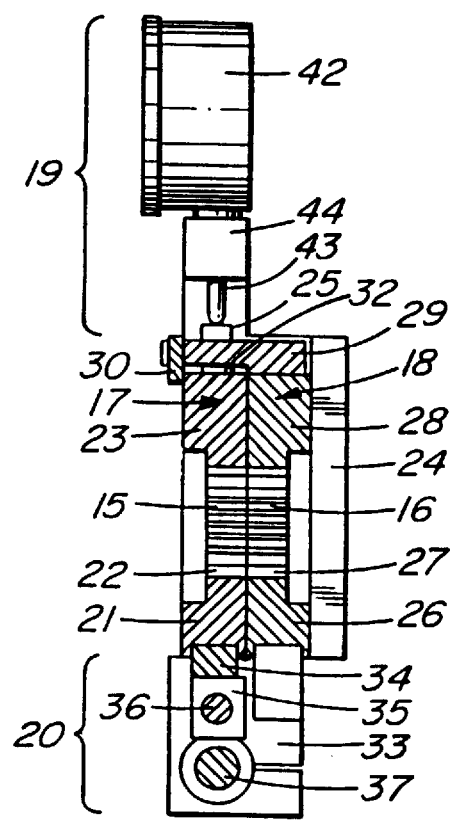
FIG. 4 is a partial sectional side view of the collimator taken on line A—A of FIG. 2.

Referring to FIGS. 2 through 4 which show a preferred embodiment of a vertically oriented collimator 12 according to the invention, the collimator shown consists generally of first and second grid assemblies 15 and 16 respectively, arranged in juxtaposition with each other and which are rigidly mounted to a moveable housing 17 and a fixed housing 18 respectively, a microbeam width indicator apparatus 19, and a micrometer adjustment apparatus 20.

The moveable housing 17 comprises a lower portion 21, and an upper portion 23 which is vertically slidably mounted on dowels (not shown) extending from the top surface 21a of the lower portion 21. Together, the upper and lower portions 23 and 21 define an orifice 22 in which is seated the first grid assembly 15. Jack screws (not shown) control the vertical sliding of the upper portion 23 along the dowels. Raising the upper portion 23 away from the lower portion 21 allows insertion of the first grid assembly 15 into the orifice 22, during assembly. When tightened, the jack screws hold the upper portion 23 tightly in place against the lower portion 21 and also serve to compress the first grid assembly 15 and hold it tightly in place. Side braces 24 which extend to the back of the apparatus are removably affixed to the sides of both the lower and upper portions 21 and 23. A cylindrical extension 25 extends from the top of the upper portion 23. The moveable housing 17 is slidably mounted to the fixed housing 18 by the "C" shaped opening defined by the side braces 24 and upper and lower portions 21 and 23 which is shaped to fit slidably around portions of the fixed housing described below.

The fixed housing 18 comprises a lower portion 26, and an upper portion 28 which is vertically slidably mounted on dowels (not shown) extending from the top surface 26a of the lower portion 26. Together, the upper and lower portions 28 and 26 define an orifice 27 in which is seated the second grid assembly 16. Jack screws (not shown) control the vertical sliding of the upper portion 28 along the dowels. Raising the upper portion 28 away from the lower portion 26 allows insertion of the second grid assembly 16 into the orifice 27, during assembly. When tightened, the jack screws hold the upper portion 28 tightly in place against the lower portion 26 and also serve to compress the second grid assembly 16 and hold it tightly in place. A top plate 29 is affixed to, or forms a part of the upper portion 28, and defines a cylindrical orifice (not shown) through which the cylindrical extension 25 extends. A front plate 30 is affixed to or forms a part of the top plate.

Figure 4A:
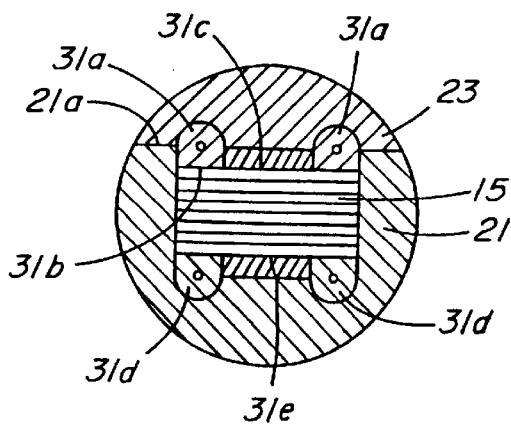
FIG. 4a is an enlarged front view of a portion of the collimator of FIG. 2 identified as B on FIG. 2, with the keepers removed.

Each of the grid assemblies 15 and 16 are held in their respective orifices 22 and 27 by keepers 31 which cover the left and right end portions of the first and second grid assemblies 15 and 16. The keepers 31 for the moveable housing 16 are removably affixed to the upper and lower portions 23 and 21. The keepers 31 of the fixed housing 17 are removably affixed to the upper and lower portions 28 and 26. Removal of the keepers 31 allows access to the orifices 22 and 27 and to the first and second grid assemblies 15 and 16. FIG. 4a shows a front view of the portion of the movable housing 17 immediately surrounding the first grid assembly 15, with the keepers 31 removed. The upper portion 23 includes two recessed extensions 31a which extend below the interface 21a between the upper portion 23 and lower portion 21. Each of these extensions includes a flat bottom 31b which bears upon the first grid assembly 15 to hold it in place. A space 31c is defined between the extensions 31a, the remainder of the upper portion 23, and the first grid assembly 15. This space may be left empty, or filled with a spacer constructed of gauge blocks, for example. Similar recesses 31d and a space 31e exist in respect of the lower portion 21. The keepers are inserted into the recesses 31a and 31d formed in the upper and lower portions 23 and 21, and are held in place with screws (not shown). The above description regarding the movable housing as illustrated in FIG. 4a may also be applied to describe corresponding portions of the fixed housing.

Springs 32 are located between the top surface of the upper portion of the moveable housing 23 and the bottom surface of the top plate of the fixed housing 29. These springs 32 serve to bias the moveable housing 17 in a downward direction against the micrometer adjustment apparatus 20.

Micrometer adjustment apparatus supports 33 are affixed to or form part of the lower portion of the fixed housing 26 to support the micrometer adjustment apparatus.

The micrometer adjustment apparatus 20 allows precise control over the movement of the moveable housing 17 relative to the fixed housing 18 and consists of an inclined plane 34, a follower 35, a follower support rod 36, a guide 37, and a micrometer screw 38. The inclined plane 34 is affixed to or forms a part of the bottom of the lower portion 21 of the moveable housing 17. The follower 35 is slidably mounted on the follower support rod 36 which itself is rigidly mounted on the micrometer adjustment apparatus supports 33. The follower 35, which has in part a tapering cross-section bears against the inclined plane 34 such that as the follower slides in a horizontal direction along the follower support rod 36, the inclined plane moves in a vertical direction, causing the moveable housing 17 to move vertically in relation to the fixed housing 18. More particularly, as the follower 35 moves left, the moveable housing 17 moves up, and as the follower moves right, the moveable housing moves down under the biasing force provided by the springs 32. The guide 37 is internally screw-threaded and is screw-mounted on to the micrometer screw 38 such that turning the micrometer screw causes the guide to move in a linear horizontal direction parallel to the length of the micrometer screw. The guide 37 seats against a groove 39 formed in the follower 35 such that movement of the guide causes a corresponding movement in the follower along the follower support rod 36. The micrometer screw 38 is rotatably mounted on to the micrometer adjustment apparatus supports 33 and comprises a knurled handle 40 extending away from the micrometer adjustment apparatus supports, and a screw-threaded portion 41 spanning the space between the micrometer adjustment apparatus supports. The net effect of the micrometer adjustment apparatus 20 is that turning of the micrometer screw 38 causes the moveable housing 17 to move vertically in relation to the fixed housing 18 thus causing mutual linear displacement of the grid assemblies 15 and 16.

The microbeam width indicator apparatus 19 consists of a microbeam width indicator 42 which is located at the top of the collimator apparatus 12 which has a sensor 43 which bears against the cylindrical extension 25 of the moveable housing 17, and an S-shaped indicator support 44 which is rigidly affixed to or forms part of the top plate 29 and which supports the microbeam width indicator.

Figure 5:
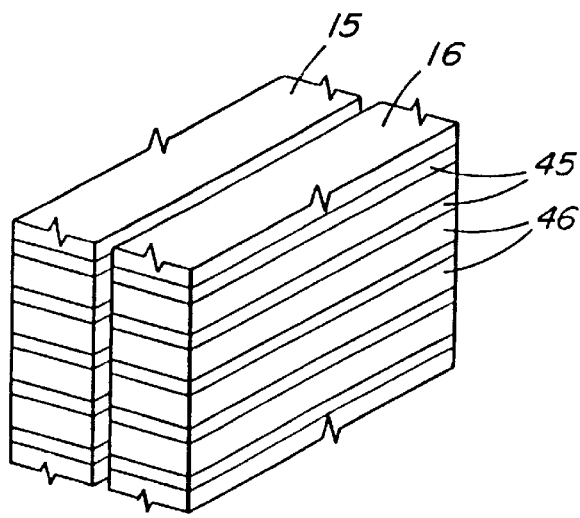
FIG. 5 is an enlarged perspective view of a portion of the grid assemblies of the collimator of FIG. 2 shown in their aligned position.
Figure 6:
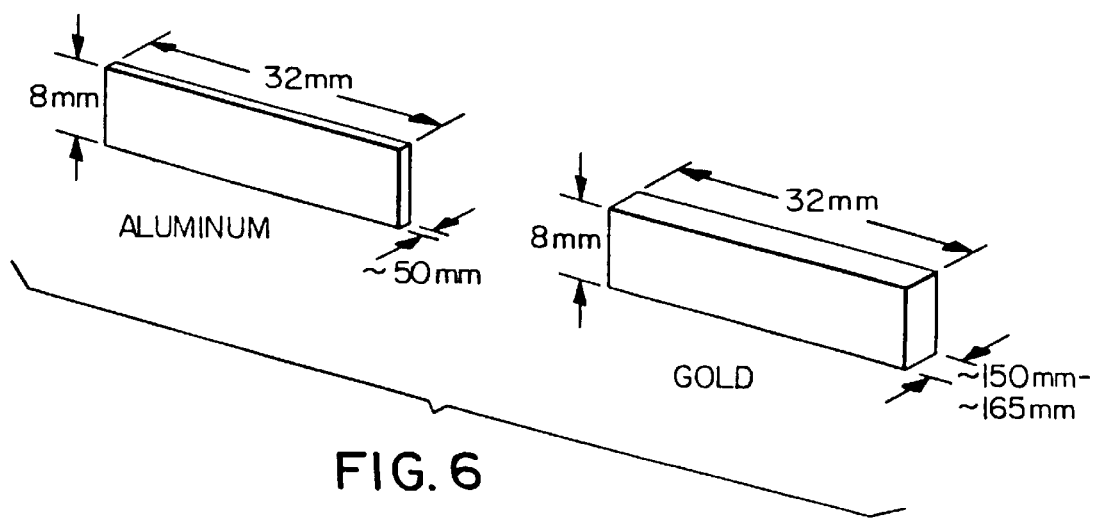
FIG. 6 is a perspective view of an aluminum leaf and a gold leaf of the collimator of FIG. 2 showing dimensions.

Referring to FIG. 5, the first and second grid assemblies 15 and 16 consist of stacks of alternating leaves 45 and 46 of materials of contrasting X-ray permeability. The grid assemblies 15 and 16 preferably comprise alternating leaves of gold and aluminum. The gold leaves 46 substantially block the passage of X-rays while the aluminum leaves 45 substantially allow X-rays to pass through. As shown in FIG. 6, each aluminum leaf 45 is 32 millimeters in length, 8 millimeters in width, and approximately 50 micrometers in thickness. Each gold leaf 46 is 32 millimeters in length, 8 millimeters in width, and approximately 150–165 micrometers in thickness. Thus, each beam formed by this prefererred embodiment has a rectangular cross-section, such cross-section having a length of 32 millimeters, and a width ranging from 0 to 50 micrometers, depending on the degree of alignment of the grid assemblies 15 and 16. In the preferred embodiment, 160 leaves are used in each of grid assemblies 15 and 16, ie. 80 gold leaves interleaved with 80 aluminum leaves.

Although gold and aluminum have been used in the preferred embodiment described above, any two materials of contrasting X-ray permeability and whose material properties allow the substances to be worked in a manner required to construct functional grid assemblies as described above, may be used. It is noted that not all materials having the required X-ray permeabilities will have the proper physical characteristics which allow very thin leaves of precise dimensions to be made. Aluminum is an example of a substance from which thin leaves of precise dimensions can easily be made, and as such is an ideal choice for the high X-ray permeability material. Gold, while being less easy to use than aluminum in that it may require more processing to achieve leaves of precise dimensions, is the best currently known choice for the low X-ray permeability material. As further examples, tungsten or platinum may be used in place of gold as the substance of low X-ray permeability, and high-temperature plastic or celluloid leaves may be used in place of aluminum as the substance of high X-ray permeability.

The widths of the leaves will depend upon the materials to be used. The widths of the leaves must be sufficient to allow the leaves made of the substance of low X-ray permeability to substantially block the flow of X-rays, while allowing the leaves made of the substance of high X-ray permeability to substantially allow the X-rays to flow through freely.

The length, and number of leaves will depend on the desired cross-sectional area for the array of microbeams, and the number of microbeams. To produce longer beams, longer leaves will be required. To produce a greater number of microbeams, more leaves will be required.

The thickness of the leaves of low X-ray permeability 46 and the leaves of high X-ray permeability 45 may also be varied to produce desired microbeam widths and distances between the microbeams.

It is important that each leaf of one grid assembly is of substantially the same thickness as its corresponding leaf in the other grid assembly. That is, in FIG. 7 which shows the grid assemblies 15 and 16 in perfect alignment, aluminum leaf 45' in one grid assembly must be the same thickness as aluminum leaf 45' in the other assembly, and gold leaf 46' must be the same thickness as gold leaf 46' in the other assembly. The same applies for aluminum leaves 45" and 45'", and for gold leaves 46" and 46'". However, it is not necessary that all leaves of one material be the same thickness. That is, in FIG. 7, aluminum leaves 45', 45" and 45'" need not be of the same thickness. The same is true of gold leaves 46', 46" and 46'".

It is also important that the leaves within each grid assembly 15 and 16 remain parallel to each other, and that the leaves of one grid assembly remain parallel to the leaves of the other.

Figure 7:
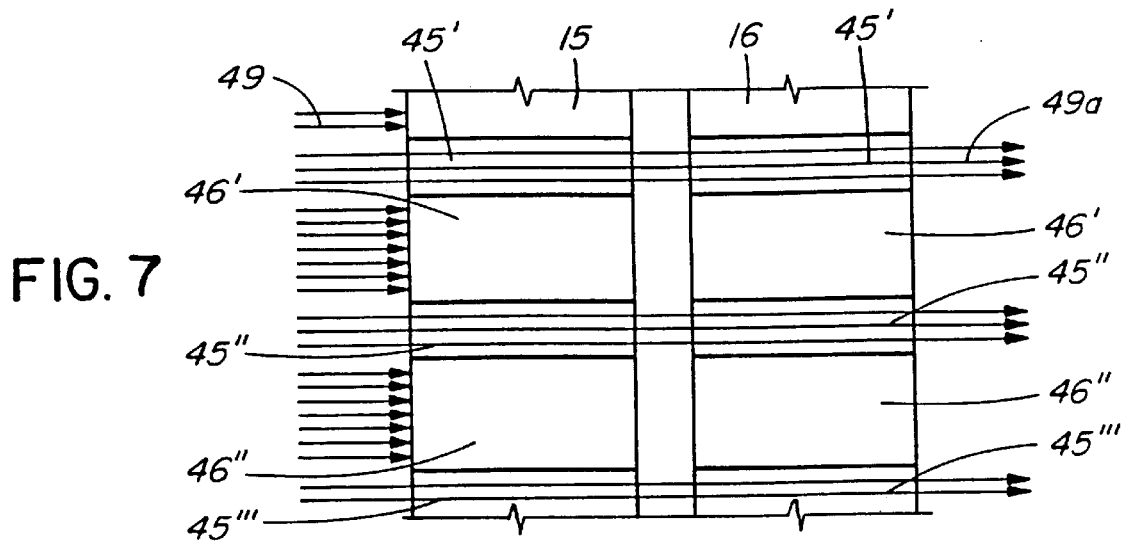
FIG. 7 is an enlarged side view of a portion of the grid assemblies of the collimator of FIG. 2 shown in their aligned position.
Figure 8:
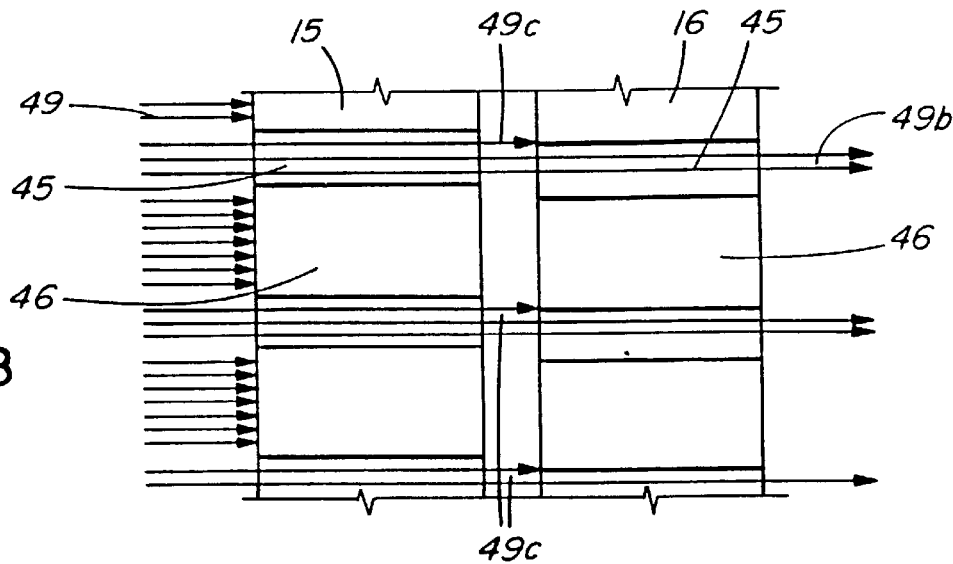
FIG. 8 is an enlarged side view of a portion of the grid assemblies of the collimator of FIG. 2 shown in a slightly offset position.

In use, the grid assemblies 15 and 16 serve to convert a wide X-ray beam into a number of non-overlapping parallel microbeams of adjustable width. The collimator apparatus 12 must be aligned with an X-ray source 10 such that the X-rays, represented by arrows 49 in FIG. 7, are parallel with the leaves 45 and 46. FIG. 7 shows a small portion of the grid assemblies 15 and 16 in their perfectly aligned position. The gold leaves, 46 substantially block the passage of X-rays while the aluminum leaves 45 allow the X-rays to pass through. In this aligned position, the maximum proportion of X-rays 49 is permitted to pass through the grid assemblies 15 and 16, and the widths of the resulting microbeams 49a are greatest. The resulting microbeams are of rectangular cross-section, and the thickness of the grid assemblies in the direction of the X-rays serve to collimate the X-rays so as to create parallel, non-overlapping microbeams. In FIG. 8, the grid assemblies 15 and 16 are slightly offset such that some of the X-rays 49c which pass through the aluminum leaves of the first grid assembly 15 are blocked by the gold leaves of the second grid assembly 16. The result is that the widths of the microbeams 49b are reduced.

The movement of the grid assemblies is controlled using the micrometer adjustment apparatus 20. By turning the micrometer screw 38, the guide 37 is moved horizontally in a direction parallel to the micrometer screw, which guide in turn moves the follower 35 along the follower support rod 36 in the same horizontal direction. This follower 35 bears against the inclined plane 34 rigidly affixed to or forming part of the moveable housing 17 such that the horizontal sliding of the follower is translated into the vertical movement of the moveable housing. In this manner, the grid assembly 15 rigidly attached to the moveable housing 17 is moved vertically relative to the grid assembly 16 rigidly attached to the fixed housing 18.

The width of the microbeams is monitored by way of the microbeam width indicator apparatus 19 which allows the user to monitor displacement of the moveable housing 17 relative to the fixed housing 18, and thus the displacement of one grid assembly 15 relative to the other 16. The indicator may be configured to display the actual width of the microbeams, to a precision as high as 0.25 micrometers.

To avoid overheating which may occur when the X-rays strike the grid assemblies 15 and 16, a cooling system (not shown) may be employed. Such a cooling system preferably circulates water through manifolds connected to each of the moveable and fixed housings 17 and 18. These manifolds do not interfere with the relative movement of the frames and may contact the grid assemblies 15 and 16 for approximately 8 millimeters at either end. Inlet and outlet hoses circulate water through the manifold.

Figure 8A:
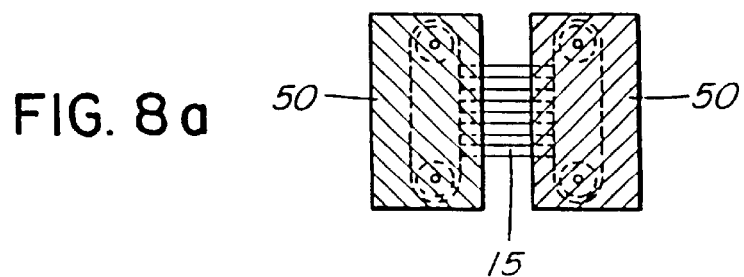
FIG. 8a is a front view of the first grid assembly of the collimator of FIG. 2 partially covered with vertical shutters.
Figure 8B:
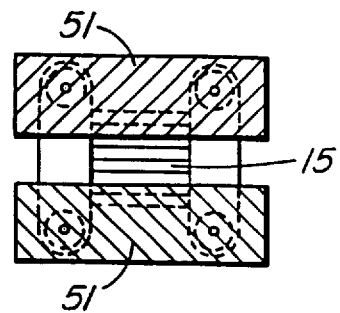
FIG. 8b is a front view of the first grid assembly of the collimator of FIG. 2 partially covered with horizontal shutters.

To control the lengths of the microbeams, or the number of microbeams, an adjustable shutter apparatus may be juxtaposed with the grid assemblies 15 and 16 either before the wide X-ray beam 11 strikes the first grid assembly 15, or after the microbeams leave the second grid assembly 16. FIG. 8a shows vertical shutters 50 slidably mounted to the movable housing 17, for movement in a horizontal direction. Horizontal movement of these vertical shutters 50 vary the lengths of the microbeams produced by the collimator apparatus. FIG. 8b shows horizontal shutters 51 slidably mounted to the movable housing 17 for movement in a vertical direction. Vertical movement of these horizontal shutters 51 vary the number of microbeams produced by the collimator apparatus. A combination of vertical and horizontal shutters may be used to control both the lengths of the microbeams, and the number of microbeams produced by the collimator apparatus. Any shutters used would be composed of a material relatively impervious to X-rays.

Although the collimator apparatus is shown in the drawings as having the capacity to adjust the width of the microbeams, it is to be understood that a static grid assembly may be used where the microbeam widths need not be adjusted. Preferably, the widths of the microbeams produced by such an apparatus are approximately 25 micrometers, and the distances between the microbeams are approximately 175 micrometers. However, other dimensions for microbeam width, and distance between microbeams are possible.

In use, it may be necessary to lubricate the movement of the moveable housing with respect to the fixed housing. The apparatus may need to be disassembled to perform this lubrication.

Numerous modifications and variations of the present invention are possible in light of the above teachings. It is therefore to be understood that within the scope of the appended claims, the invention may be practised otherwise than as specifically described herein.

In the illustrated embodiments, springs 32 have been used between the moveable housing 17 and the fixed housing 18. Of course, it is to be understood that any suitable resilient connection could be used, elastics for example.

Although the microbeam width indicator is shown in the illustrated embodiments as a dial, it is to be understood that any form of suitable analog or digital indicator may be used, a linear analog indicator for example.

Figure 9:
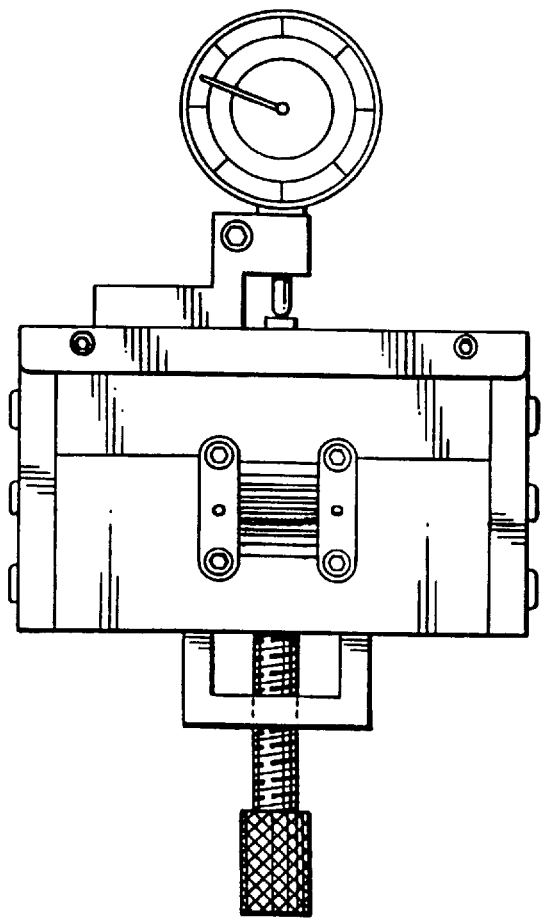
FIG. 9 is a front view of another embodiment of the invention.

The micrometer adjustment apparatus shown in the illustrated embodiments may be replaced by any other suitable adjustment mechanism, a direct screw adjustment mechanism as shown in FIG. 9, for example.

A very specific apparatus for holding the grid assemblies in place has been described, but it is to be understood that any suitable apparatus could be used.

The embodiments of the invention in which an exclusive property or privilege is claimed are defined as follows:

1. An adjustable collimator for producing non-overlapping parallel microbeams of radiation from a single wide beam of radiation comprising:
   a) first and second grid assemblies arranged in juxtaposition with each other, each comprising a plurality of alternating parallel leaves of low and high X-ray permeability, each leaf of said first grid assembly being of the same thickness as the corresponding leaf of said second grid assembly;
   b) supporting means by which each of said grid assemblies is rigidly supported such that the leaves of each grid assembly are held parallel to one another, and the leaves of the first grid assembly remains parallel to the leaves of the second grid assembly; and
   c) adjustment means by which the grid assemblies may be precisely mutually displaced in a linear direction perpendicular to the leaves of the grid assemblies,
   whereby the leaves of low X-ray permeability substantially block the passage of X-rays while the leaves of high X-ray permeability substantially allow the X-rays to pass through resulting in a plurality of non-overlapping parallel microbeams whose widths may be adjusted by the adjustment means.

2. The adjustable collimator according to claim 1 further comprising an indicator for displaying microbeam width.

3. The adjustable collimator according to claim 2 wherein the indicator is a dial.

4. The adjustable collimator according to claim 1 wherein said supporting means comprises a moveable housing for rigidly supporting the first grid assembly and a fixed housing for rigidly supporting the second grid assembly, said moveable housing being slidably mounted to the fixed housing.

5. The adjustable collimator according to claim 4 wherein the adjustment means comprises a micrometer screw which controls the movement of a follower, said follower being slidably attached to the fixed housing for movement in a direction parallel to the leaves of the grid assembly, said follower bearing against an inclined plane rigidly attached to or forming part of the moveable housing, said moveable housing being borne against said follower by a resilient means.

6. The adjustable collimator according to claim 5 wherein said resilient means comprises springs.

7. The adjustable collimator according to claim 4 further comprising an indicator for displaying microbeam width.

8. The adjustable collimator according to claim 5 further comprising an indicator for displaying microbeam width.

9. The adjustable collimator according to claim 7 wherein said indicator senses linear displacement, said indicator being rigidly attached to the fixed housing while a displacement sensor of the indicator bears against the moveable housing.

10. The adjustable collimator according to claim 9 wherein said fixed housing includes a top plate defining an aperture, and said displacement sensor of the indicator bears against an extension of the moveable housing protruding through said aperture.

11. The adjustable collimator according to claim 7 wherein the indicator is a dial.

12. The adjustable collimator according to claim 1 wherein the leaves of low X-ray permeability are made of gold.

13. The adjustable collimator according to claim 1 wherein the leaves of high X-ray permeability are made of aluminum.

14. The adjustable collimator according to claim 1 wherein the leaves of low X-ray permeability are made of gold and the leaves of high X-ray permeability are made of aluminum.

15. The adjustable collimator according to claim 8 wherein the leaves of low X-ray permeability are made of gold and the leaves of high X-ray permeability are made of aluminum.

16. The adjustable collimator according to claim 1 wherein the leaves of low X-ray permeability are 32 millimeters in length, 8 millimeters in width, and approximately 150 to 165 micrometers in thickness.

17. The adjustable collimator according to claim 1 wherein the leaves of high X-ray permeability are 32 millimeters in length, 8 millimeters in width, and approximately 50 micrometers in thickness.

18. The adjustable collimator according to claim 1 wherein the first and second grid assemblies are each comprised of 160 alternating leaves of low and high X-ray permeability.

19. The adjustable collimator according to claim 1 wherein a cooling system is used to keep the collimator cool.

20. The adjustable collimator according to claim 1 further comprising a shutter apparatus for adjustably varying at least one of, the lengths of the microbeams, and the number of the microbeams.

21. A collimator for producing non-overlapping parallel microbeams of radiation from a single wide beam of radiation comprising:
(a) a grid assembly comprising a plurality of alternating parallel leaves of low and high X-ray permeability; and
(b) supporting means by which said grid assembly is rigidly supported such that the leaves of the grid assembly are held parallel to one another,
whereby the leaves of low X-ray permeability substantially block the passage of X-rays while the leaves of high X-ray permeability substantially allow the X-rays to pass through resulting in a plurality of non-overlapping parallel microbeams.

22. The collimator according to claim 21 wherein the leaves of low X-ray permeability are made of gold, and the leaves of high X-ray permeability are made of aluminum.

23. The collimator according to claim 21 wherein the leaves of low X-ray permeability are 175 micrometers in thickness, and the leaves of high X-ray permeability are 25 micrometers in thickness.

24. The collimator according to claim 22 wherein the gold leaves are 175 micrometers in thickness, and the aluminum leaves are 25 micrometers in thickness.

* * * * *